United States Patent [19]

Dupont et al.

[11] Patent Number: 5,001,284

[45] Date of Patent: Mar. 19, 1991

[54] PROCESS FOR MANUFACTURING FATTY ALCOHOLS

[75] Inventors: René Dupont, Nogent-sur-Marne; Laurent Ferenczi; Guy Simonet, both of Paris, all of France

[73] Assignee: L'Air Liquide, Societe Anonyme Pour L'Etude Et L'Exploitation Des Procedes Georges Claude, Paris, France

[21] Appl. No.: 420,461

[22] Filed: Oct. 12, 1989

[30] Foreign Application Priority Data

Oct. 18, 1988 [FR] France ............................... 8813074

[51] Int. Cl.⁵ .................. C07C 29/136; C07C 31/125; C07C 31/04
[52] U.S. Cl. .................................... 568/885; 252/373; 422/187; 423/648.1
[58] Field of Search ........................................... 568/885

[56] References Cited

U.S. PATENT DOCUMENTS

| 2,156,217 | 4/1939 | Andrews et al. | 568/885 |
| 2,844,633 | 7/1958 | Braconier et al. | 568/885 |
| 3,179,500 | 4/1965 | Bowen et al. | 252/373.1 |
| 3,650,713 | 3/1972 | Chinchen et al. | 252/373.1 |

FOREIGN PATENT DOCUMENTS

| 207359 | 4/1956 | Australia | 568/885 |
| 558703 | 6/1958 | Canada | 568/885 |
| 783661 | 9/1957 | United Kingdom | 568/885 |
| 3409 | 10/1983 | World Int. Prop. O. | 568/885 |

Primary Examiner—J. E. Evans
Attorney, Agent, or Firm—Young & Thompson

[57] ABSTRACT

In a process for manufacturing fatty alcohols comprising hydrogenating the corresponding fatty acid methyl esters, the hydrogen used for the hydrogenation reaction is regenerated from impure methanol as a by-product of the reaction. The impure methanol recovered from the hydrogenation reactor is conducted to a steam reformer reactor, from whence the regenerated hydrogen is recycled back to the hydrogenation reactor.

4 Claims, 1 Drawing Sheet

PROCESS FOR MANUFACTURING FATTY ALCOHOLS

The present invention relates to a process for producing fatty alcohol.

The production of fatty alcohol from methyl esters is carried out in a hydrogenation reactor in accordance with the reaction (A)

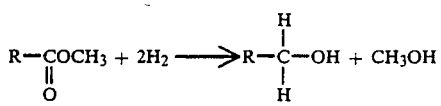

The fatty alcohols produced are then separated from the methanol-containing residue, the latter being constituted principally by methanol and higher alcohols.

Then this residue is treated either by combustion in a furnace or by flare burning it, or purified by distillation when pure methanol is needed on the industrial site or there are possibilities of commercialization of the methanol. However, the distillation results in expenditures of energy and losses of methanol mainly due to the entrainment thereof in the water at the bottom of the column.

Moreover, the hydrogen required for the reaction is either produced on the site by various processes, such as cracking or reforming of hydrocarbons, electrolysis, etc., or comes from an outside source.

Figure 1:
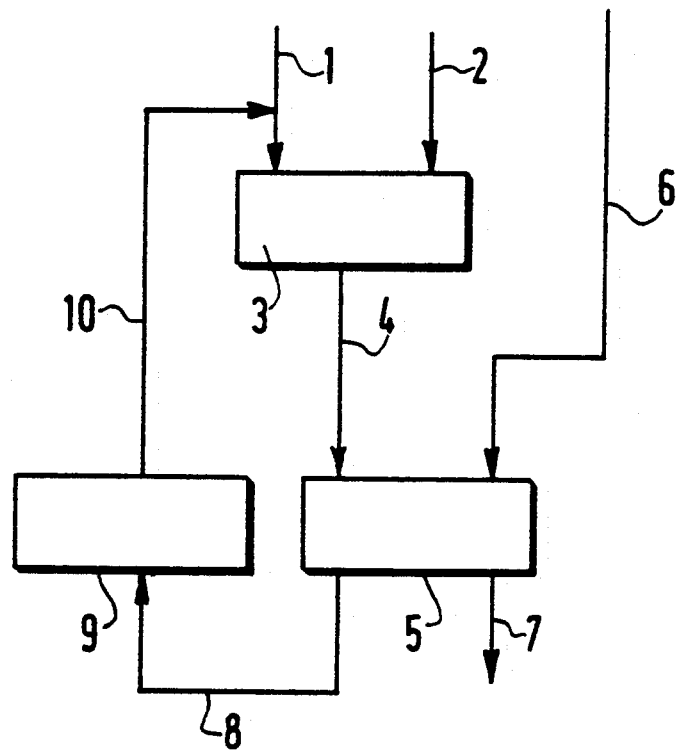

The fatty alcohols which are obtained from fatty plant materials, are produced in two steps or according to two production lines, namely cross esterification and hydrogenation. to FIG. 1 of the accompanying drawing which represents a functional diagram, the supply liquids, the methanol and the fatty materials, are introduced through the circuits (1) and (2) to the cross esterification (3), the first step in the production of the methyl esters directly conducted through the circuit (4) to the hydrogenation stage (5) fed with hydrogen through the pipe (6). In the course of the second production step, the methyl esters in the presence of hydrogen are converted in accordance with the reaction (A) into fatty alcohols collected at (7) and the residual methanol, or impure methanol, is conducted through the circuit (8) to the rectification by distillation stage at (9) and the purified methanol is recycled through the circuit (10) with a supply (1) of methanol.

On sites which themselves produce all of the methyl esters to be hydrogenated, the needs in pure methanol are in principle at least equal to the quantity obtainable by distillation of the impure methanol. However, the expenditures of energy, the losses and the pollutions related to the distillation requires the research of a better valorization of the impure methanol.

Furthermore, a number of sites import the esters to be hydrogenated and their need in pure methanol becomes less than their production of impure methanol. Depending on the market value of methanol, the distillation may be found to be uneconomical and the purified product unsaleable.

Further, a process has been sought for manufacturing fatty alcohols by hydrogenation of methyl esters without recycling the impure methanol in the form of pure methanol to the inlet of a possible production of esters.

It is proposed to carry out the reaction of hydrogenation of the methyl esters jointly with a reaction of steam reforming of methanol.

The impure methanol issuing from the reaction of the hydrogenation of the methyl esters is subjected to the steam reforming reaction and the hydrogen obtained in this way is recycled to the inlet of the fatty alcohol production line.

The procedure resides in recycling the impure methanol not in the form of pure methanol at the inlet of the ester production line but in the form of hydrogen for the hydrogenation line.

This recycling permits rendering the two steps for producing fatty alcohol from fatty plant materials, independent under good economical conditions.

The independence of the two production lines: cross esterification and hydrogenation, provide industrials with the possibility of dividing the functions of the production of esters and the production of alcohols in the best way between their different sites in plant oil-producing countries and in fatty alcohol-consuming countries.

The reforming process associated with the hydrogenation of the methyl esters is of any type of the steam reforming of impure methanol. In particular, a reforming at low temperature and the process for the reforming of impure methanol as disclosed in the patent application FR 87 15006 in the name of the applicant is well adapted. According to this process of the reforming of impure methanol containing alcohols higher than the methanol, in which the heat is supplied by means of a heat-conveying fluid heated by the residual gas, of a purification of the gas produced by reforming, for producing pure hydrogen, there is achieved a simultaneous combustion of the condensed water-alcohol mixture coming from the cooling of the reformed gas, on one hand, and from the residual gas coming from the purification of the hydrogen, on the other hand.

According to a variant, in the case where the methanol contains heavy impurities, after having allowed the mixture to stand for a suitable period of time, the mixture: water+impure methanol is filtered so as to separate out the solid phase, and the filtered liquid is fed to the reforming unit.

Figure 2:
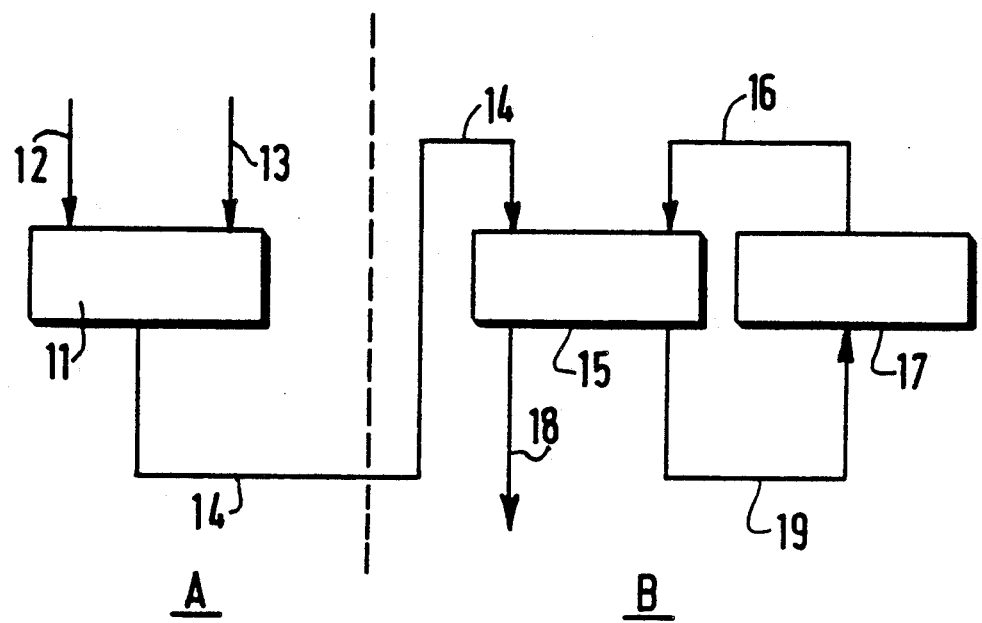

The process according to the invention may be carried out in a plant having two independent production lines of the type shown in FIG. 2.

The production line A mainly comprises a cross esterification reactor (11) in which the reaction of the methanol and the fatty materials introduced at (12) and (13) is carried out, after cross esterification under conditions conventional in this technique, the methyl esters produced are drawn off through the circuit (14) and sent to the production line B.

This second production line B mainly comprises a hydrogenation reactor (15) fed with methyl esters (14) coming from the production line A and with pure hydrogen recycled through (16) and coming from the steam reforming (17), the fatty alcohols formed by the hydrogenation are separated and drawn off at (18) and the impure methanol is conducted through the circuit (19) to the steam reforming (17).

A comparative study of the expenditures of energy of the two possible treatments of the impure methanol shows the advantages of the proposed process. This comparison is carried out on a simple site where the two cross esterification and hydrogenation operations are carried out in a balanced manner.

The impure methanol issuing from the hydrogenation reactors has a composition which varies with the treated esters. The considered tonnage represents the quantity of pure methanol contained in the methanol-+impurities mixtures.

Let us consider a factory producing 20,000 t/year of fatty alcohols from 22,000 t/year of methyl esters. The needs in hydrogen are about 250 Nm3 per metric ton of treated esters, namely 5,500,000 Nm3/year. The quantity of impure methanol given off is 4,500 t/year.

According to the conventional method, the impure methanol is distilled and the hydrogen is produced by steam reforming of natural gas whose consumption is 0.5 Nm3 of natural gas per Nm3 of hydrogen. The expenditure of energy expressed in equivalent metric tons of petroleum or tep (with the equivalence 1 toe=1,1000 Nm3 of natural gas) is the following: (toe=(metric) ton oil equivalent)

| Heat needs of the distillation: | |
| --- | --- |
| 160 Nm3 of natural gas per metric ton of distilled methanol, namely: | 650 toe |
| Losses of methanol (entrainment in the water at the bottom of the column, losses by distillation, etc.) 12% of the charge. | |
| In valorizing the methanol at its lower heating power, namely 0.54 toe/ton, the loss represents | 290 toe |
| Production of hydrogen: | 2,500 toe |
| Total Expenditure: | 3,440 toe |

According to the invention, the hydrogenation reaction is carried out jointly with the reforming of the impure methanol. The reforming of the impure methanol furnishes the necessary quantity of hydrogen. The reforming is autothermal and the sole expenditure of energy results from the 4,500 t of new methanol which must be in introduced at the inlet of the cross esterification. With the same valorization of the methanol, there is obtained:

Total Expenditure: 2,450 toe
The saving in energy is therefore about 1,000 toe

Apart from the savings in energy, the process permits, relative to the conventional method, a lower investment expenditure: saving as concerns the methanol distillation column and the hydrogen production unit since a reforming of the methanol is usually less costly than a reforming of natural gas (lower temperature and simpler process).

The process is applicable in the so-called natural fatty alcohol industry.

These alcohols are employed in the formulation of detergents, cosmetics, additives, etc.

In a general way, any industry consuming hydrogen and producing methanol, impure or not, may employ this process.

We claim:

1. A process for manufacturing fatty alcohols, comprising hydrogenating fatty acid methyl esters to produce fatty alcohols and impure methanol, wherein said hydrogenating step is carried out using hydrogen gas regenerated from said impure methanol in a separate steam reforming operation.

2. A process according to claim 1, wherein said hydrogenating step comprises feeding a hydrogenation reactor with said fatty acid methyl esters and with hydrogen generated by a unit for steam reforming impure methanol, separating and drawing off the fatty alcohols formed by said hydrogenating step, feeding the impure methanol obtained in the hydrogenation reaction into said steam reforming unit and recycling the regenerated hydrogen produced in said reforming unit to said hydrogenation reactor.

3. A process according to claim 2, comprising, in the reforming of impure methanol containing alcohols higher than methanol, supplying heat by means of a heat-conveying fluid heated by the residual gas, of a purification of the gas produced by reforming, thereby obtaining pure hydrogen, cooling the reformed gas, and effecting a simultaneous combustion of a condensed water-alcohol mixture coming from the cooling of the reformed gas and from the residual gas coming from the purification of hydrogen.

4. A process according to claim 3, comprising, in the reforming of impure methanol containing impurities, allowing the water+impure methanol mixture containing impurities to stand for a suitable period of time, and thereafter filtering said water+impure methanol mixture so as to separate out a solid phase thereof, and feeding the filtered liquid to the steam reforming unit.

* * * * *